United States Patent [19]

Heran et al.

[11] Patent Number: 4,646,362
[45] Date of Patent: Mar. 3, 1987

[54] DISPOSABLE UNDERPANTS, SUCH AS CHILD'S TRAINING PANTS AND THE LIKE

[75] Inventors: William M. Heran; Glen R. Fleischer; Joyce A. Damico, all of Neenah; Paul T. Van Gompel, Hortonville, all of Wis.

[73] Assignee: Kimberly-Clark Corporation, Neenah, Wis.

[21] Appl. No.: 807,900

[22] Filed: Dec. 16, 1985

Related U.S. Application Data

[63] Continuation-in-part of Ser. No. 690,351, Jan. 10, 1985.

[51] Int. Cl.$^4$ .......................... A41B 9/00; A61F 13/16
[52] U.S. Cl. .......................... 2/400; 2/403; 604/392; 604/385 A
[58] Field of Search .................. 2/400, 401, 402, 403, 2/406; 604/385.2, 392

[56] References Cited

U.S. PATENT DOCUMENTS

| | | | |
|---|---|---|---|
| 3,424,162 | 1/1969 | Parravicini | 2/400 X |
| 4,205,679 | 6/1980 | Repke et al. | 604/385.2 |
| 4,258,440 | 3/1981 | McGowan | 2/403 X |
| 4,352,356 | 10/1982 | Tong | 604/392 X |

Primary Examiner—Werner H. Schroeder
Assistant Examiner—Judith L. Olds
Attorney, Agent, or Firm—Douglas L. Miller; Donald L. Traut; Jeremiah J. Duggan

[57] ABSTRACT

A disposable underpant (10, 10') comprising a front panel (11) and rear panel (12) joined together along side seams (13) to provide a three-dimensional garment having a pair of elasticized leg openings (14) and an elasticized waist opening (15), and including a bodyside liner (16), outer cover (17) and absorbent batt (18) therebetween, in which the outer cover (17) has an inner layer (30) of plastic material and an outer layer (31) of nonwoven fibrous material.

19 Claims, 9 Drawing Figures

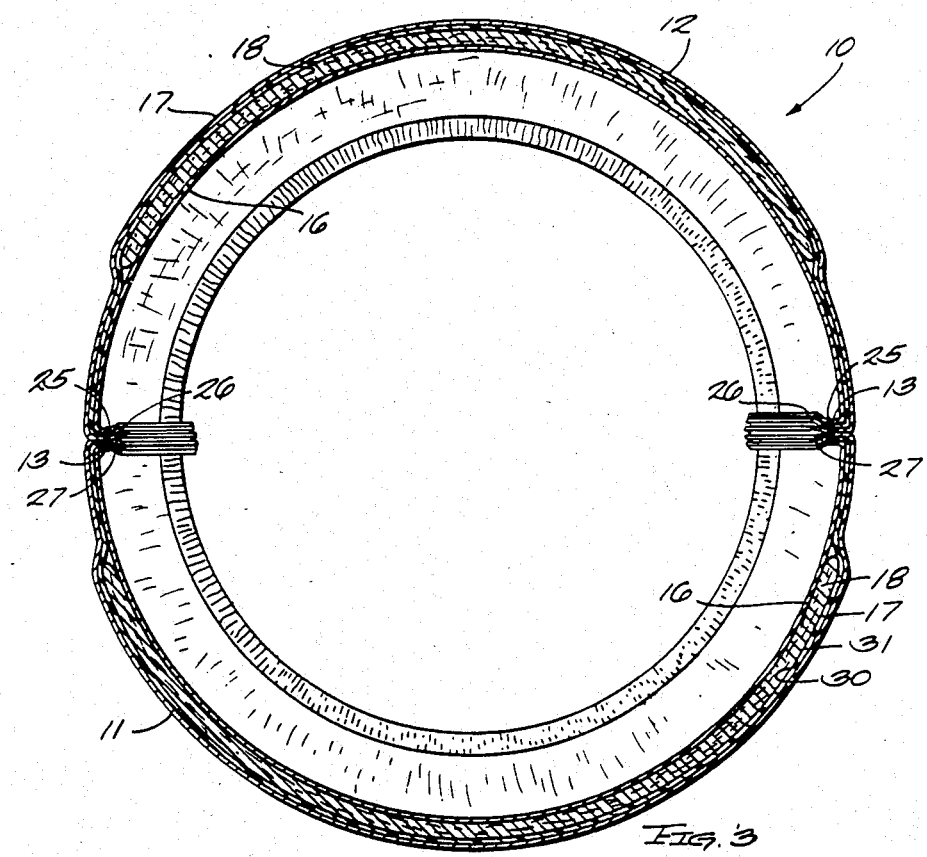
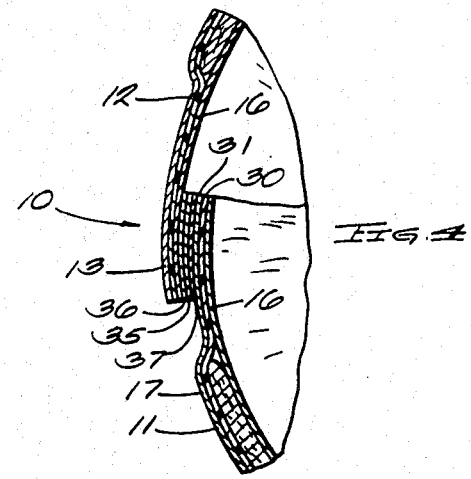

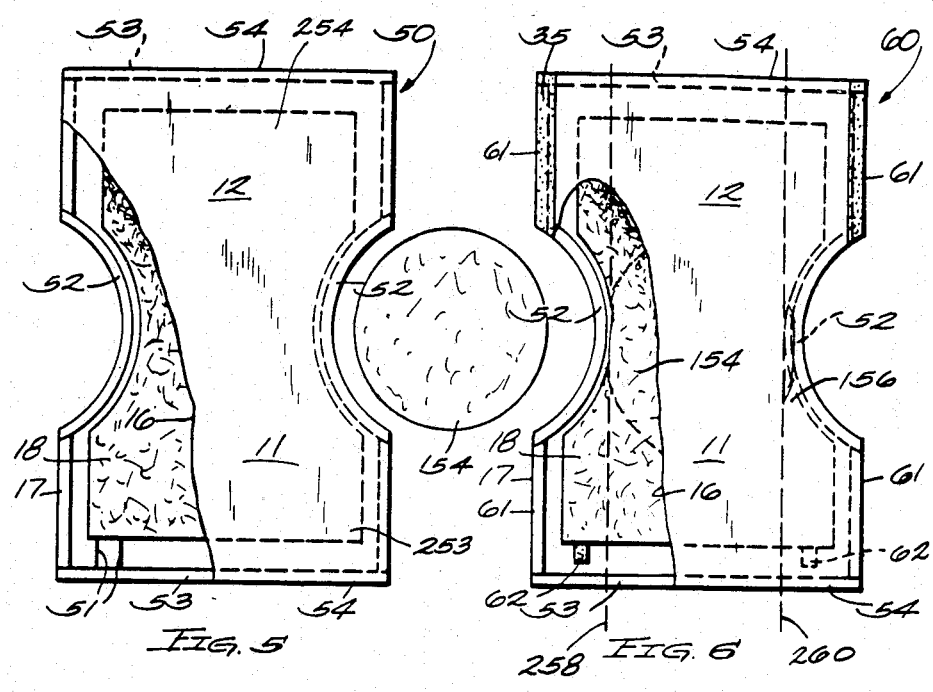
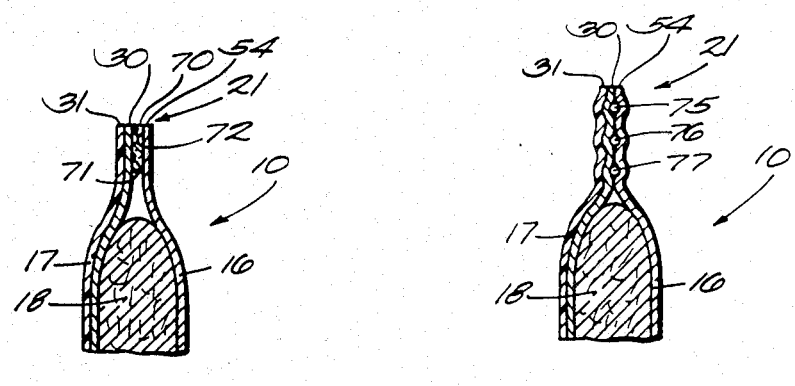

DISPOSABLE UNDERPANTS, SUCH AS CHILD'S TRAINING PANTS AND THE LIKE

This application is a continuation-in-part of application Ser. No. 690,351, filed Jan. 10, 1985.

TECHNICAL FIELD

This invention relates generally to the field of disposable underpants having elasticized leg and waist openings, particularly disposable child's training pants and similar garments.

BACKGROUND ART

Disposable diapers, as is well known, now find widespread use for infant care and have generally replaced the use of cloth diapers. The typical disposable diaper is a three-layer composite structure comprising a liquid permeable bodyside inner liner, a liquid impermeable outer cover and an absorbent batt sandwiched between the liner and the cover. Materials now in general use for the three principal elements of a disposable diaper include various types of nonwoven fabrics for the bodyside liner, a thin thermoplastic film for the outer cover and cellulosic fluff for the absorbent batt.

Disposable diapers of the type presently on the market are flat open-sided garments that are intended to be fit about an infant by a parent while the infant is lying down. The rear panel of the diaper is placed underneath the infant, and the front panel drawn between the infant's legs, after which the sides are overlapped and held together by pressure sensitive adhesive tape. A diaper is meant for use when the child is young and dependent upon a parent for this essential purpose.

The popularity of disposable diapers has led us to believe there is a demand for a disposable underpant, such as a disposable training pant that can be used when a child grows out of a diaper. Diapers are typically used with infants up to about fifteen months old. When a child reaches an age in the range of about fifteen to thirty months, however, a parent generally desires to start toilet training so that the child can become independent of a parent. The training pant is intended for use when the child has reached an age at which he or she is ready to graduate to an underpant type of garment as a replacement for disposable diapers previously used. Thus, a suitable training pant must be a garment having closed sides so that a child can raise and lower it as necessary without requiring the aid of a parent. At the same time, a training pant must provide features of liquid and solid absorbency and prevent leakage of the waste fluids.

Cloth training pants, although widely used, have disadvantages. Current cloth training pants have very little absorbency and often must be used with exterior rubber or plastic pants. When a child wets a cloth training pant, most often all of the child's clothes must be changed. Further, if a child has a bowel movement, it is difficult to remove a cloth pant without making a mess, and the pant must be soaked and bleached. All of these factors can make the toilet training process frustrating for both child and parent.

In addition, it is believed that the psychology of the toilet training stage is such that the child should perceive he or she is graduating to a garment that is different than a disposable diaper. The requirements for a disposable underpant such as a training pant are not satisfactorily met by the constructions of disposable diapers as currently known in the art. In this connection, for example, the typical disposable diaper, as stated previously, has an outer layer comprising a liquid impermeable sheet of plastic film. Various techniques have been used to give the plastic sheet the feel and appearance of texture, but the exterior of the garment has a plastic feel or appearance which is closely associated with the concept of a diaper but would be inappropriate for a disposable training pant. Since the purpose of a training pant is to encourage the child to make the transition from diapers to washable or reusable cloth underpants, it is important that a disposable training pant simulate a cloth underpant as much as possible.

The need for a disposable training pant or similar underpant capable of meeting the demand for this type of garment has been the impetus for the development of the present invention.

SUMMARY OF THE INVENTION

Our present invention provides a disposable underpant, particularly a disposable training pant, comprising a three-dimensional garment having closed side seams, an elasticized waist opening and elasticized leg openings, and including a bodyside liner and outer cover with an absorbent batt sandwiched therebetween, wherein the outer cover is a two layer composite material providing the dual characteristics of liquid imperviousness and a clothlike appearance. This structure provides a disposable undergarment which is perceived as protective underwear for a child rather than a diaper associated for use by an infant.

An undergarment to be suitable for use in toilet training children or by incontinent children or adults should comprise (a) a nonwoven fabric cover having a front portion, a rear portion and a crotch portion connecting the front and rear portions, both side margins of the front portion being joined to respective side margins of the rear portion so as to define a three-dimensional undergarment having a pair of leg openings and a waist opening; (b) a liquid pervious inner liner and an absorbent batt between the liner and the fabric cover, a first elastic means extending about one leg opening, a second elastic means extending about the other leg opening, and a third elastic means extending about the waist opening.

DESCRIPTION OF THE DRAWINGS

FIG. 3 is a horizontal sectional view of the disposable underpant of FIG. 1;

FIG. 4 is a partial horizontal sectional view similar to FIG. 3 illustrating an alternate form of side seam for the disposable underpant of FIG. 1;

FIG. 5 is a plan view, with portions broken away illustrating a flat blank as suitable for producing the underpant of FIG. 1;

FIG. 6 is a plan view, with portions broken away, illustrating another form of flat blank suitable for producing the underpant of FIG. 1;

FIG. 7 is a partial sectional view illustrating one form of elasticized leg and/or waist opening of the underpant of FIG. 1;

FIG. 8 is a partial sectional view illustrating another form of elasticized leg and/or waist opening for the underpant of FIG. 1.

DETAILED DESCRIPTION OF THE INVENTION

Figure 1:
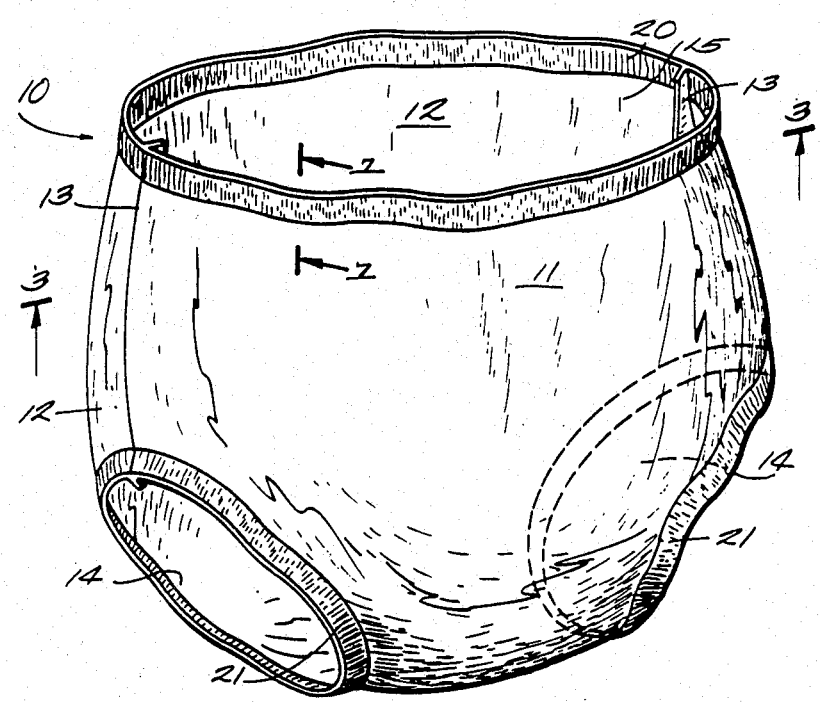
FIG. 1 is a perspective view of a disposable underpant according to the present invention.
Figures 2, 9:
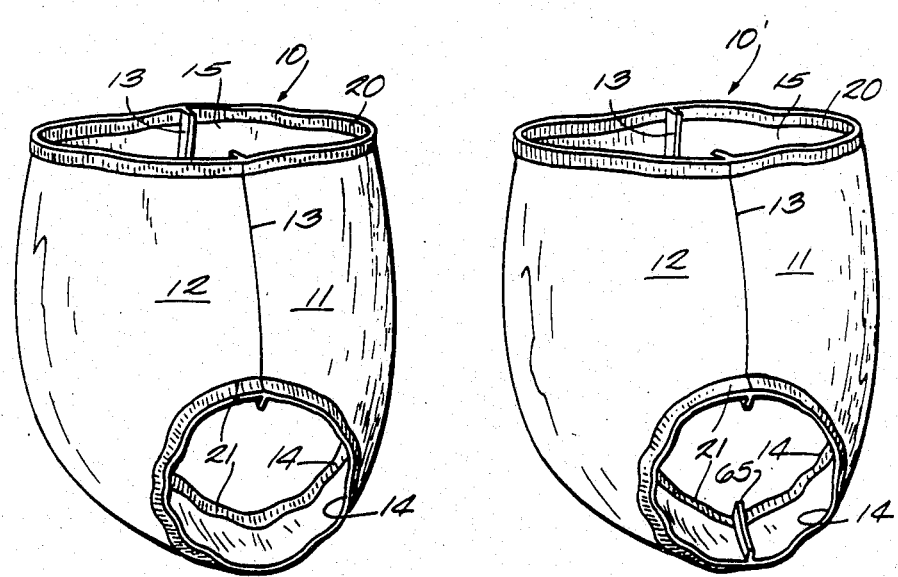
FIG. 2 is a side perspective view of the disposable underpant of FIG. 1.
FIG. 9 is a side perspective view of an alternate form of the disposable panty of FIG. 1.

FIGS. 1 and 2 illustrate, in front and side perspective views respectively, a disposable underpant 10 constructed in accordance with the present invention. The underpant 10 includes a front panel 11 and a rear panel 12 joined together alongside seams 13 to form a three-dimensional garment with closed sides having a pair of leg openings 14 and a waist opening 15. Referring now to FIG. 3, the underpant 10 includes a moisture pervious bodyside liner 16, a moisture impervious outer cover 17, and an absorbent batt 18 positioned between the liner 16 and outer cover 17. The absorbent batt may be secured to either the bodyside liner or the outer cover, or both, by any suitable means well known in the art such as lines or other patterns of adhesive, pressure sensitive tapes, heat seals, sonic seals, etc.

Referring again to FIG. 1, the waist opening 15 of the underpant 10 is surrounded by a circumferential elasticized band 20 and each leg opening 14 is surrounded by a circumferential elasticized band 21. Suitable constructions for the elasticized bands 20 and 21 are described in further detail later in this description.

The bodyside liner 16 can be any flexible porous sheet which passes fluids therethrough, i.e. a moisture pervious material, to be absorbed by the absorbent batt 18. The liner may comprise a nonwoven web or sheet of polyolefin fibers, such as polypropylene or polyethylene, or polyester fibers; a web of spun bonded polypropylene, polyethylene or polyester fibers; a web of rayon fibers; a bonded carded web of synthetic or natural fibers, or a mixture of synthetic and natural fibers, and the like. Further the liner 16 may also comprise a plastic film which is perforated or apertured to obtain the desired degree of moisture perviousness, and may also comprise an expanded plastic webbing material or a scrim material. The bodyside liner 16 preferably is made of a material which will feel soft and comfortable against the skin of an infant or adult.

The absorbent batt 18 may comprise any suitable material capable of absorbing and retaining waste fluids that pass through the liner 16. Thus, the absorbent batt may comprise cellulosic material such as an air-formed batt of wood pulp fibers, commonly known as "fluff"; a batt of melt blown synthetic fibers, such as macrofibers or microfibers, of polypropylene, polyethylene, polyester and the like; a bonded carded web of synthetic or cellulosic fibrous materials; a composite of melt blown fibers, such as macrofibers or microfibers of polypropylene, polyethylene polyester or the like mixed with pulp fibers; or a blend of fluff with staple textile fibers such as rayon and the like. Preferably the batt should contain a high hardwood pulp content since this increases the fine microfiber pore structure in meltblown and similar batts and therefore improves absorbency and liquid retention. The batt may comprise one or more layers or combinations of the foregoing materials.

Preferably, the batt may include compounds added to increase its absorbency. The material selected for the absorbent batt most usefully has an absorbent capacity in the range of about 30 to 550 grams of synthetic urine retained at 0.5 psi. For a disposable training pant intended for infant use after the diaper stage, the absorbent capacity of the batt is preferably in the range of about 350 to 500 grams of synthetic urine retained at 0.5 psi. Furthermore, it is desirable that the underpant 10 not present a diaper appearance and the absorbent batt therefore most usefully comprises a low bulk, high absorbency material. Preferably the batt will contain a three-dimensional dispersion of particles of water insoluble hydrocolloid polymer. The superabsorbent is preferably dispersed uniformly in a three-dimensional configuration within the voids of the fibrous batt but in the region which is closest to the outer fabric cover, so that liquids contacting the batt penetrate freely within the batt to superabsorbent particles farthest from the skin of the wearer. There are several types of superabsorbent materials that are commercially available:

a. Grafted starch b. Starch polyacrylic acid grafted copolymer c. Grafted cellulose—(CMC) carboxy—methyl cellulose d. Modified PVA (polyvinyl Alcohols), and preferably e. Polyacrylic acid salts that are crosslinked to form absorbent polymers such as Water-Loch J-500 (Acquakeep OSH) produced by Seitetsu in Japan.

Preferably the tensile strength of the absorbent batt should be from about 1.75 psi to about 5.00 psi. Also preferably, the burst strength of the absorbent batt should range from about 250 ergs/cm$^2$ to about 550 ergs/cm$^2$ dry and from about 300 ergs/cm$^2$ to about 500 ergs/cm$^2$ wet.

Preferably the absorbent batt is formed having an outwardly bulging crotch portion. By contouring the batt in a manner providing the bulge in the crotch, the undergarment has a significantly greater amount of absorbent material in the crotch portion for improved protection from leakage in an area where it is most needed. In addition, advantageously decreasing the amount and thickness of the absorbent material upon approaching the periphery of the absorbent batt and the undergarment, i.e. in the longitudinal or end edges 54 and 53, provides increased discreetness for the wearer. The undergarment will not have a tendency to stick out during use. Additionally, it is preferable that the absorbent batt be shaped such that when applied to the outer cover the absorbent batt should be absent in the ear portion, i.e., the portions of the outer cover lying outside the longitudinal line extending from the innermost portion of the curved leg opening, since the undergarment does not require absorbency in this region and absence of the absorbent material provides for a more discreet fit on the wearer and does not stick out during use.

Preferably, the undergarment is formed such that the traverse measurement of the crotch section of the absorbent batt is less than about 3 inches. More preferably the traverse measurement of the overall diaper is less than about 4 inches. The thickness in the bulge portion of the absorbent batt in the crotch portion is preferably about 1.5 to 5 times the thickness of the absorbent material located in the front and rear portions of the absorbent batt. Preferably the thickness of the absorbent batt in the crotch portion is about 2 times the thickness of the absorbent material in the front and rear portions. Preferably during the formation of the absorbent batt a web of absorbent is cut traversely with a generally elliptically shaped cutout being made in the leg area. This leg area ellipse is folded over onto the top of the crotch portion. The ellipse is shown in FIG. 5 as 154; the ellipse is then placed atop the absorbent batt in FIG. 6 in crotch region 156. Preferably the traverse width of the absorbent material in the crotch portion is ¼ of the sum of the widest traverse measurements of the front and rear portions. Forming an absorbent batt in this configuration eliminates the need for a waste of the absorbent material while unexpectedly forming an absorbent batt that provides additional absorbency in the needed areas and proper sizing about the waist.

Preferably the leg area ellipse is sized such that it covers at least 30 percent, more preferably 50 percent of the absorbent batt and is biased in size toward the front of the training pant.

In accordance with a highly preferred aspect of this invention, the outer cover 17 performs the dual functionality of providing moisture imperviousness and also providing a textile feel and look for the underpant 10. For this purpose, referring now to FIG. 3, the outer cover 17 comprises a two-layer composite material having an inner layer 30 and an outer layer 31. The inner layer 30 is a layer or stratum of plastic material which provides a moisture barrier or liquid imperviousness.

Suitable plastic materials for the inner layer 30 are polyolefin polymers such as polyethylene or polypropylene; polyolefin copolymers such as ethylene vinyl acetate, ethylene methyl acrylate or ethylene ethyl acrylate; polyvinyl chloride; nylon; or other thermoplastic materials capable of providing liquid imperviousness. The inner layer 30 of the outer cover should provide a sufficient degree of liquid imperviousness to prevent or preclude waste fluids from striking through or penetrating through the outer cover The outer layer 32 of the cover 17 most preferably consists of a layer of nonwoven fibrous material. Materials suitable for the outer layer 31 include a spun-bonded nonwoven web of synthetic fibers such as polypropylene, polyethylene or polyester fibers; a nonwoven web of cellulosic fibers, textile fibers such as rayon fibers, cotton and the like, or a blend of cellulosic and textile fibers; a spun-bonded nonwoven web of synthetic fibers such as polypropylene, polyethylene or polyester fibers mixed with cellulosic, pulp fibers or textile fibers; or melt blown thermoplastic fibers, such as macrofibers or microfibers, of polypropylene, polyethylene, polyester or other thermoplastic materials or mixtures of such thermoplastic macrofibers or microfibers with cellulosic, pulp or textile fibers.

The inner layer 30 and outer layer 31 of the cover 17 are advantageously bonded to one another, by any means appropriate for the specific materials selected for the two layers. The two layers can be laminated using heat or pressure or both heat and pressure. The two layers can also be bonded with adhesive, heat sealing or ultrasonic sealing. In addition, thermoplastic polymeric material of the inner layer 30 can be extrusion coated onto the nonwoven outer layer 31. If desired, the textile effect of the nonwoven outer layer 31 can be further enhanced by various embossing patterns.

FIG. 3 illustrates one form of side seams 13 for the underpant 10 that is made by seaming together inturned contacting side edge portions of the outer layer 31 of the outer cover 17 of the front and rear panels. This provides a narrow fin seam, which can be made relatively narrow such as about 3/16 to ½ inch wide so as to minimize the amount of seam located inside the garment. The seams 13 between the inturned contacting side edge portions of the outer cover can be formed by any suitable means well known in the art appropriate to the specified material employed for the outer layer 31 of the cover; thus, sonic sealing, heat sealing, adhesive bonding, and the like are appropriate techniques. FIG. 4 illustrates an alternate construction for the side seams 13 wherein side edge portions of the garment are overlapped and joined together with an adhesive element 35 coated on both of its opposed surfaces with layers 36 and 37 of pressure sensitive adhesive. In this alternate embodiment, a side edge portion of the bodyside inner liner 16 of the rear panel 12 is bonded to a side edge portion of the outer layer 31 of the outer cover of the front panel 11 of the underpant 10. Sonic sealing and heat sealing techniques also can be used to bond the overlapped portions as shown in FIG. 4. Other side seam constructions effective to form a garment having closed sides can be employed to form the underpant 10, and sewn side seams may be of interest such as for some types of adult underpants.

An especially useful construction for the side seams 13 is a manually tearable or tearaway seam. This can be obtained by bonding the contacting side edge portions along a narrow bond within the side seam portions. A bond strength of about 2000 grams/inch of seam length (as measured on an appropriate instrument such as an Instron tensile tester) is suitable for providing a tearaway seam but which is also strong enough to hold the garment together. One way to make a seam of this type is to bond the contacting side portions by suitably controlled sonic sealing along a narrow bond portion that is about ⅛" wide. A tearaway seam is a highly advantageous and preferred feature because a parent can manually tear the side seams apart in order to remove the underpant from a child; this is particularly helpful when the underpant is quite soiled and removal in the normal fashion would be messy. A manually tearaway seam can be with both the inturned fin style seams illustrated in FIG. 3 or the overlapped seam of FIG. 4. Another important consideration in forming a strong bond which provides for a tearaway feature includes selection of a suitable material for the cover. Propropylene, ethylene vinyl acrylate, ethylene ethyl acrylate and ethylene methyl acrylate are preferred. Polyethylene is not preferred but ethylene methyl acrylate copolymers of ethylene may be used.

The side seams 13 in FIG. 3 are shown as incorporating another useful structural feature. The inturned contacting side edge portions of the garment are joined together along a narrow bond portion 25 that is spaced from the free ends 26 of the side edge portions. This provides a side seam having a flap portion 27 inside the garment along which the side edge portions are not bonded together so as to be free of one another. Any bond portion, such as formed by sonic sealing, heat sealing or adhesive bonding, will be relatively stiff. The flap portion 27 acts as a cushion between a person's body and the stiff bond portion 25, thereby enhancing the comfort or wearability of the underpant 10. It has been found that a bond portion about 1/16" to ⅛" wide and a flap portion about ⅛" to ⅜" wide are suitable for this purpose and provide a fin seam that will not irritate an infant or adult wearing the underpant 10.

The underpant 10 can be expeditiously manufactured from a blank cut to a suitable configuration. An appropriate blank 50 is illustrated in FIG. 5. A sheet of material for the outer cover 17 is cut to an hourglass configuration having arcuate cutouts defining the leg openings of the garment Absorbent batt 18, also cut to an hourglass configuration with arcuate leg cutouts, is placed on top of the outer cover in the desired position, and may be secured thereto by spaced parallel glue lines 51. Preferably the batt is shaped such that the extensions of the batt in the areas outside longitudinal lines 258 and 260 in FIG. 6 extending from the traverse edge of the inside crotch portion is limited. An arcuate elastic means 52 is positioned around each leg cutout and preferably, as explained below, positioned along the outer edge of the cover 17 along the cutout portion. Linear elastic means 53 are positioned along each end 54 of the blank, which will form the elastic means for the waist portion of the finished garment. As indicated in FIG. 5, the elastic means 52 are positioned closely adjacent the nearby edge of the absorbent batt so as to provide a form fitting panty type of garment instead of being spaced from the batt to have a web of material between the elastic means and the batt as is common with some disposable diapers. Next, a sheet of bodyside inner liner 16, also cut to an hourglass configuration, is placed over the assembly of the outer cover and the batt. Both the liner 16 and cover 17 have superimposed marginal portions which project beyond the margin of the batt 18, and the liner and cover may be joined together with elastics 52 and 53 within the superimposed marginal portions. After being fully assembled, the blank 50 is folded along its central transverse area and the sides of the front and rear panels are seamed together as illustrated in FIG. 3 to form the finished underpant 10.

FIG. 6 illustrates a blank 60 suitable for producing underpant 10 having side seams of the type illustrated in FIG. 4. Most elements of the blank 60 are the same as those of the blank 50 and the corresponding elements are therefore numbered with the same reference numerals. Blank 60 includes an adhesive element 35 of two-side coated pressure sensitive adhesive tape along each side edge portion 61 of the rear panel 12. Thus (see especially FIG. 4) adhesive layer 36 of each element 35 is adhered to a side marginal portion of the outer cover of the rear panel 12. To produce the underpant 10 from the blank 60, the blank is folded along its transverse medial portion and the side edge portions 61 of the front panel are joined together to the layer 37 of pressure sensitive adhesive of each element 35 in the manner shown in FIG. 4. The blank 60 also shows an alternate form of securing the absorbent batt 18 by use of two side pressure sensitive adhesive elements 62 between the batt and outer cover 17.

FIG. 9 illustrates an alternate system for construction of the underpant of the present invention wherein the underpant 10' includes a separate front panel 11 and rear panel 12 that are joined together along central crotch seam 65. The remaining elements of the underpant 10' are the same as in underpant 10 and the common elements are identified with the corresponding reference numerals employed in FIG. 1. FIG. 9 represents an alternative method for constructing the underpants of the present invention as compared to making the underpants with the folded blanks 50 and 60 of FIGS. 5 and 6.

FIGS. 7 and 8 illustrate particularly useful forms of elastic means for use at the leg openings and waist opening of the underpant 10. The elastic means constructions of FIGS. 7 and 8 are as described and claimed in the commonly assigned co-pending patent application of Ales et al. entitled "Elastic Form-Fitting Closure Constructions for Disposable Garments," filed on Jan. 10, 1985, U.S. Ser. No. 690,348, the disclosure which is incorporated herein by reference. As shown in FIG. 7, elastic means 54 comprises a strip of elastic material 70 having opposed surfaces 71 and 72, wherein surface 71 is bonded to closely spaced bond points along an edge portion of the inner layer 30 of the outer cover 17 and surface 72 is bonded to an edge portion of the interior surface of the bodyside liner 16. Further, the outer edges of the liner 16, cover 17, and elastic strip 70 are contiguous with one another. The elastic strip 70 is bonded to the liner 16 and cover 17 along the entire area of its surfaces 71 and 72 when applied thereto in an elongated or stretched condition; upon retraction of the elastic strip 70, micro-buckling of the outer cover between bond points results in an elasticized waist or leg opening which has a smooth yet finely ribbed or pleated appearance. FIG. 7 is a sectional view of the elasticized band 21 around the leg openings of the garment 10, and the elasticized band 20 around the waist opening can be of the same structure.

The construction illustrated in FIG. 8 is similar to that of FIG. 7 except that the elastic means 53 comprises a plurality of spaced parallel strands 75, 76 and 77 of elastic material, each strand having a circular cross section, as described and claimed in the commonly assigned co-pending application of Ales et al. entitled "Disposable Garment with Multiple Strand Elasticized Openings," U.S. Ser. No. 690,349, the disclosure of which is incorporated herein by reference. The elastic means construction of FIG. 8 can be used either for the circumferential elasticized band 20 around the waist opening of the underpant or the elasticized bands 21 around the leg openings 14 of the underpant, or both; a presently preferred embodiment of the underpant 10 is to employ the elastic means construction of FIG. 7 for the circumferential band 20 about the waist opening and the elastic means construction of FIG. 8 for the elasticized band 21 of the leg openings with a good seal against leakage of fluids therethrough. The underpant 10, however, can be constructed with other types of elasticized bands at the waist opening and the leg openings, such as, for example, a strip of elastic material intermittently bonded or sewn to either the outer cover 17 or inner liner 16, or both, along the waist opening and leg openings Preferably the elastic means about the waist and/or the legs is at least two ribbons or ropes. Also, the elastic means can be contiguous with the outer edges of the liner and cover along the elasticized openings as shown in FIGS. 7 and 8, or it can be spaced inwardly thereof; in the latter instance, it is preferred that the elastic means be spaced only slightly inwardly of the edges of the garment if it is desired to avoid a gathered look about the leg and waist openings.

The tension measurement found useful was determined by stretching the leg opening to 10.5 inches for the small training pant (20–29 pounds) and 11.5 inches for the medium training pant (30–39 pounds), holding for five minutes and then measuring the tension in grams. A similar procedure was followed for the waist except the opening was stretched to 18.5 inches for the small and 19.5 inches for the large. These stretching distances were determined as being the average leg and waist size for the wearer of the small training pant and the medium training pant. Preferably the tension exerted by the elastic means in the leg area ranges from about 165 to about 220 grams, more preferably from about 180 to about 200 grams. The elastic means about the leg opening preferably comprises at least two elastic members where the tension on the member closer to the absorbent batt is greater than the tension on the elastic member further from the absorbent batt. More preferably the ratio of the tension on the members is from about 4:3 to about 3:2. In the waist region the preferred tension is from about 330 to about 400 grams and more preferably from about 360 to about 380 grams.

Any suitable elastomeric material can be employed for the elastic means 52 and 53 that exhibits at least an elongation (defined herein as $L_s - L_r/L_r$ where $L_s$ is the stretched length of an elastic element and $L_r$ is retracted length, multiplied by 100 to obtain percent elongation) in the range of 5% to 300% preferably in the range of 25% to 200%. Further along these lines, there may be some preferential vagaries in respect of the elasticity of these elastic means relative to the geometry elected by the designer For example, within the preferred range mentioned above, it has been determined that a most preferred range for the leg elastic is from about 80 to about 110 for rope elastic and about 40 to about 70 for ribbon elastic. Also for the waist elastic the preferred range is from about 200 to about 250 for rope elastic and about 60 to about 200 for ribbon elastic. Preferably the elastic has a spring constant of from about 5 to about 40 gms/cm and more preferably from about 15 to about 22 gms/cm.

Various commercially available materials can be used, such as natural rubber, butyl rubber or other synthetic rubber, urethane elastomeric material such as that available from B. F. Goodrich Company under the trademark TUFTANE, and elastomeric material available from the H.B. Fuller Company under the tradename FULLASTIC. The latter material (see e.g. U.S. Pat. No. 4,418,123) is based upon thermoplastic elastomeric copolymers of the A-B-A type such as those available from Shell Chemical under the trademark KRATON which have a rubbery midblock such as butadiene or isoprene and polystyrene end blocks, and is especially useful because it is a self-adhesive material and can be applied to the layers of the garment without additional adhesive between the elastic means and the layers. The elastic means can be applied to the garment by any suitable means including adhesive bonding, heat sealing or sonic bonding, whichever is appropriate to the specific material selected for the elastic means.

Adhesion of the elastics 20 and 21 to the liner 16 and to the cover 17 is improved by addition of a dissimilar polymer to the liner/cover material. This is illustrated by addition of polypropylene to an ethylene methyl acrylate cover. It has been convenient to add the dissimilar polymer by addition of a yellow colorant Ampacet containing a yellow pigment and a polypropylene binder. This addition has been found particularly effective in EMA when a Fullastic self adhering elastic is used in the training pant.

Preferably, the front and back of the training pant are designated as such so as to permit the wearer to properly dress himself. This may be suitably accomplished by a label on the interior of the rear portion of the training pant.

EXAMPLE

A disposable panty 10 as illustrated in FIG. 1 was constructed in a size suitable for use as an infant's training panty with an elasticized waist opening as shown in FIG. 7, elasticized leg openings as shown in FIG. 8 and tearaway side seams. The material of the outer cover, or exterior panel, of the disposable underpant was a two-layer composite web having an outer layer of nonwoven polypropylene fibers and an inner layer of ethylene methyl acrylate extrusion coated onto the nonwoven fibrous outer layer. The panty had an interior panel comprising a bodyside liner of spun bonded polypropylene fibers. An absorbent batt of a composite of polypropylene microfibers and cellulosic fibers was sandwiched between the exterior panel and the interior panel. Testing of the panty established that it combined the features of liquid-imperviousness due to the plastic inner layer of the outer cover and a clothlike appearance because of the fibrous outer layer of the outer cover. A useful disposable training pant was thereby provided that is expected to be well received by parents and of a type that will aid and encourage children going through the toilet training stage.

There has thus been described a disposable underpant including an outer cover constructed of two layers of different materials wherein the inner layer is a plastic material capable of providing the desired degree of moisture imperviousness and the outer layer is a nonwoven fibrous material capable of presenting a clothlike or textile appearance and feel to the underpant. It is believed that the new underpant herein described provides a construction that is an improvement over similar garments of the prior art and that it may therefore extend the use of disposable underpants, particularly as a training pant for a child who is ready to graduate from the diaper stage. The texture and feel, as well as the fit and absorbent capabilities, of the present underpant provide a disposable undergarment that can function to contain waste fluids and at the same time present a clothlike appearance which could encourage an infant to discontinue use of diapers. The foregoing disposable underpant can be more absorbent than a cloth training pant and does not require an additional protective rubber or plastic covering pant. Because the present garment has elasticized waist and leg openings, a young child of an appropriate age can readily raise and lower the underpant and thereby become accustomed to using the toilet without being dependent upon the aid of a parent. The neat tailored look of the present underpant should be of aid in promoting the use of the training pant in lieu of a diaper. Other important potential uses for the underpant herein described and claimed are an adult menstrual garment or an adult incontinence garment. The same factors come into play in these end uses, since a clothlike disposable underpant having an attractive tailored look is provided that should be particularly attractive for an adult.

The present invention has been described hereinabove by reference to several specific embodiments, but it is expected that those skilled in the art of manufacturing disposable garments will be able to devise modifications of the exemplary embodiments and it is intended that the appended claims encompass any such obvious modifications which are within the true spirit and scope of the present invention.

We claim:

1. A three-dimensional disposable underpant for wearing about a portion of the body, comprising:
    a disposable liquid pervious inner bodyside liner having opposed marginal side edges,
    a disposable liquid impervious outer cover having a front portion, a rear portion, a crotch portion and opposed marginal side edges, and being generally superimposed over said liquid pervious inner bodyside liner,
    an absorbent batt including a front portion, a rear portion, and a crotch portion generally corresponding to said disposable liquid impervious outer cover, and disposed between said liquid pervious inner bodyside liner and said liquid impervious outer cover, said liquid pervious inner bodyside liner and said liquid impervious outer cover having respective portions of their marginal side edges joined together to form a pair of side seams, a waist opening, and a pair of leg openings, and elastic means extending about said openings for providing elasticity thereto, said liquid impervious outer cover including an inner layer of liquid impervious plastic material adjacent said absorbent batt and an outer layer of nonwoven fibrous material substantially superimposed over and contiguous with said inner layer.

2. The underpant of claim 1 wherein the transverse measurement of said crotch portion of said absorbent batt is less than about three inches.

3. The underpant of claim 1 wherein the transverse width of absorbent material in said crotch portion is ¼ of the sum of the widest transverse measurements of said front and said rear portions.

4. The underpant of claim 1 wherein the thickness of said absorbent batt in said crotch portion is from about 1.5 to about 5 times the thickness of said absorbent batt in said front and said rear portions.

5. The underpant of claim 1 wherein said absorbent batt is outwardly bulging in said crotch portion.

6. The underpant of claim 1 wherein said absorbent batt is attached to said outer cover.

7. The underpant of claim 1 wherein said absorbent batt comprises a superabsorbent.

8. The underpant of claim 7 wherein said superabsorbent is confined to a predetermined region within said absorbent batt.

9. The underpant of claim 7 wherein said superabsorbent is disposed in a layer of said absorbent batt immediately adjacent to said outer cover.

10. The underpant of claim 1 wherein said elastic means about a respective said leg opening comprises at least two elastic members, wherein the tension of said elastic member closest to said absorbent batt is greater than the tension of said elastic member furthest from said absorbent batt.

11. The underpant of claim 10 wherein the ratio of the tension on said closest elastic member to said furthest elastic member is from about 4:3 to about 3:2.

12. The underpant of claim 10 wherein the tension on said leg opening elastic means ranges from about 165 to about 220 grams.

13. The underpant of claim 12 wherein the tension on said leg opening elastic means ranges from about 180 to about 200 grams.

14. The underpant of claim 1 wherein the tension on said elastic means about said waist opening ranges from about 330 to about 450 grams.

15. The underpant of claim 14 wherein the tension on said waist opening elastic means ranges from about 360 to about 380 grams.

16. The underpant of claim 1 wherein said outer cover comprises a non-stretchable material.

17. The underpant of claim 1 wherein said outer cover comprises a stretchable material.

18. The underpant of claim 1 wherein said absorbent batt is substantially absent from front and rear panels transversely extending beyond a longitudinal line extending from outside transverse edges of said crotch portion.

19. The underpant of claim 1 wherein said abosorbent batt comprises a material having a dry tensile strength ranging from about 250 ergs/cm$^2$ to about 550 ergs/cm$^2$.

* * * * *